Figure 1:
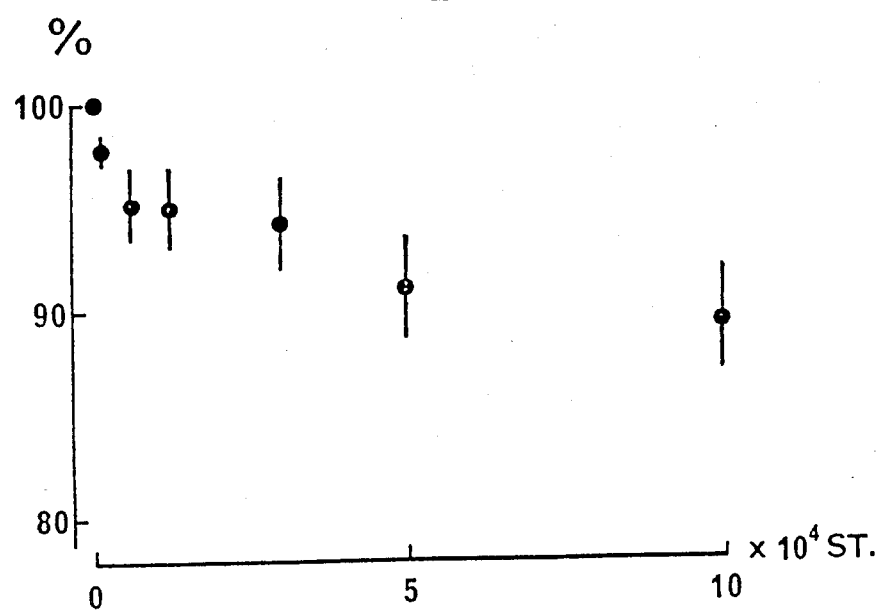

United States Patent [19]

Maetani et al.

[11] Patent Number: 4,504,228

[45] Date of Patent: Mar. 12, 1985

[54] DENTAL CASTING

[75] Inventors: Teruo Maetani; Ryoichi Miyoshi; Yukinori Nahara; Yasuyuki Kawazoe; Taizo Hamada, all of Hiroshima, Japan

[73] Assignee: Daikin Kogyo Co., Ltd., Japan

[21] Appl. No.: 356,510

[22] Filed: Mar. 9, 1982

[51] Int. Cl.³ .............................................. A61K 6/08
[52] U.S. Cl. ...................................... 433/199; 427/2; 428/422; 428/461; 433/201; 433/202; 433/217; 433/222
[58] Field of Search .................... 427/2; 433/200, 201, 433/199, 207, 217, 222, 228, 171; 428/422, 461; 523/115–118; 525/189

[56] References Cited

U.S. PATENT DOCUMENTS

| | | | |
|---|---|---|---|
| 3,154,506 | 10/1964 | Janssens | 428/422 |
| 3,304,216 | 2/1967 | Eggleton | 428/422 |
| 3,981,945 | 9/1976 | Attwood et al. | 525/189 |
| 3,992,725 | 11/1976 | Homsy | 106/35 |
| 4,139,576 | 2/1979 | Yoshimura et al. | 525/189 |

Primary Examiner—Lorenzo B. Hayes
Attorney, Agent, or Firm—Larson and Taylor

[57] ABSTRACT

A dental casting coated with a tetrafluoroethylene polymer shows suppressed accumulation and easy removability of the plaque, and excellent mechanical endurance.

9 Claims, 6 Drawing Figures

BEFORE ABRASION

AFTER ABRASION

NON COATING

PTFE COATING

DENTAL CASTING

This invention relates to a dental casting and a method of preventing the plaque accumulation on the dental casting.

It has well demonstrated that there is a relationship between the plaque accumulation and surface properties of dental casting. Especially, the surface roughness plays an important role in plaque accumulation, i.e., the more surface roughness becomes, the more plaque accumulates. However, clinical observations have clearly shown that the plaque accumulates easily on any smoothed surface of dental castings because of their high surface energy and plaque adhesiveness. Moreover, in the case of teeth with crown or bridge, plaque is well retained on the proximal and cervical surfaces, and the bottom of pontic, which are not easily cleaned merely by brushing or any other cleaning method. There is, therefore, a great need for prevention of the plaque accumulation on dental casting by modification of their surface properties.

An object of this invention is to provide a dental casting which effectively prevents the plaque accumulation.

Another object of this invention is to provide a dental casting in which the plaque, if accumulated, is easily removed by gargle, etc.

Still another object of this invention is to provide a dental casting having excellent mechanical properties.

These and other objects of this invention will become apparent from the following description.

This invention provides a dental casting which is coated with a tetrafluoroethylene polymer and a method of preventing the plaque accumulation with use of the dental casting.

Inventors of the invention have investigated the mechanical and microbial properties of tetrafluoroethylene polymer (hereinafter referred to as "PTFE") coating on metallic dental casting and have found that the plaque accumulation is suppressed by PTFE coating and the accumulated plaque is easily removed by a running tap water. Further, the dental casting of the invention has been confirmed to have an excellent mechanical endurance and to stand long use.

Examples of useful dental castings of the invention to be coated are those made from a metal alloy, for example, Au alloys such as Au-Pd alloy, Au-Pt alloy; Ag alloys; Co alloys; Cr alloys such as Cr-Ni alloy.

In the invention, the dental casting is coated with PTFE. PTFE is preferably employed together with an adhesive binder. Examples of useful binder are polyamide, polyimide, polyamideimide, epoxy resin, alkyd resin, silicon resin, polyether, polyethersulfone, polysulfone and polyphenylene sulfide. The binder is used in an amount of usually about 0.1 to about 20 parts by weight, preferably about 0.3 to about 8 parts by weight per one part by weight of PTFE. PTFE and the binder are preferably used in a form of an organic or aqueous solution. The solution is prepared with use of a solvent such as water or organic solvent, for example, methylcarbitol, ethylcarbitol, butylcarbitol, ethylcellosolve, butylcellosolve, methyl isobutyl ketone, methyl ethyl ketone, xylene, toluene, isopropyl alcohol, N-methylpyrrolidone.

Prior to coating, the dental casting is usually polished in a conventional manner and is sandblasted, and then degreased under ultrasonication. PTFE is coated on the dental casting in a thickness of usually about 0.5 to about 20 $\mu$m, preferably about 1 to about 5 $\mu$m after baking. PTFE is coated by a usual manner such as dipping, brushing, spraying, etc. To ensure a uniform layer of PTFE coating, PTFE is preferably sprayed by a pencil typed spray gun under air pressure. The coated film is then dried at preferably about room temperature to about 120° C., baked at preferably below about 400° C., and then cooled preferably as soon as possible after the baking.

The invention will be described below in greater detail with reference to the following examples and test examples, in which the part and % are all by weight.

EXAMPLE 1

Metal specimens of Au-Pd alloy (Cast Well, G-C Dental Co., Ltd., Japan) were sandblasted with aluminum oxide of 100 mesh under air pressure at 5 kg/cm$^2$, and were then cleaned with acetone under ultrasonication.

PTFE coating composition was prepared by uniformly mixing the following ingredients.

30% PTFE organosol in methyl isobutyl ketone: 380 parts

60% Epoxy resin liquid solution (PZ-985E, Chiba Geigy Co., Ltd.): 260 parts

20% Epoxy resin hardener liquid solution (HZ-985E, Chiba Geigy Co., Ltd.): 90 parts In an effort to ensure an uniform layer of PTFE coating, the PTFE coating composition was sprayed by a pencil typed spray gun (Hand Piece HP-C3, Iwata Toso Co., Ltd., Japan) having a nozzle diameter of 0.3 mm under air pressure of 2 kg/cm$^2$. After spraying, the coated layer was dried by infrared lamp at 80° C. for 15 min. and then baked in an electrical oven at 180° C. for 30 min. to obtain a coating layer of 4 $\mu$m in thickness. The final step of this procedure involved the specimen being cooled in water as soon as possible after the baking.

EXAMPLE 2

Same metal specimens previously treated as in Example 1 were similarly coated with a PTFE coating composition prepared by uniformly mixing the following ingredients.

30% PTFE organosol in methyl isobutyl ketone: 300 parts 27.5% Polyamideimide resin liquid solution (HI-600, Hitachi Chemical Co., Ltd.): 330 parts N-Methylpyrrolidone: 280 parts The coated layer was dried by infrared lamp and then baked at 280° C. for 30 min.

EXAMPLE 3

Same metal specimens previously treated as in Example 1 were similarly coated with a PTFE coating composition obtained by uniformly mixing the following ingredients.

30% PTFE organosol in methyl isobutyl ketone: 270 parts

50% Silicon resin liquid solution (SR-2115, Toray Silicone Co., Ltd.): 450 parts Silicon resin hardener (SR-2115R, Toray Silicone Co., Ltd.): 70 parts Methyl isobutyl ketone: 167 parts The coated layer was dried by infrared lamp and then baked at 100° C. for 30 min.

TEST EXAMPLE 1

Abrasion test of PTFE coating

Figure 2:
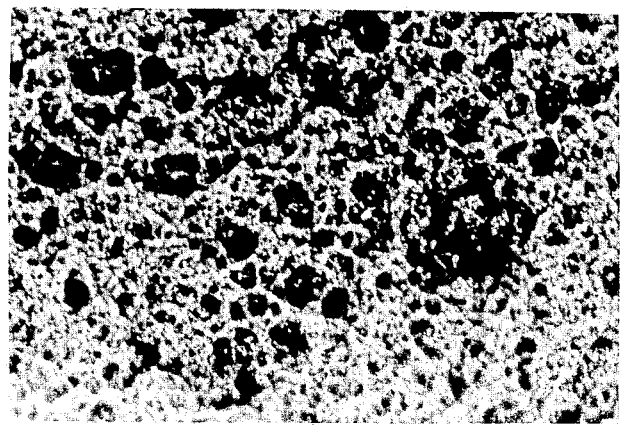
Figure 2:
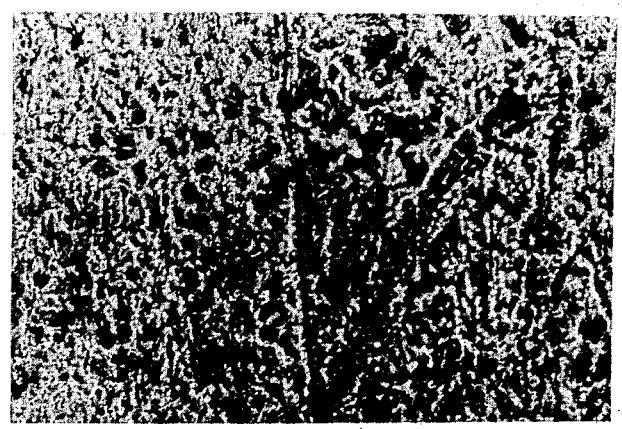

In order to evaluate the mechanical endurance of PTFE coating, an abrasion test was carried out using a brushing device (Dental Abrasion Machine, Fukuda Seisakusho Co., Ltd., Japan). The metal specimens (10×20×1.5 mm) coated with PTFE obtained in Example 1 were placed in the brushing device and were abrassed by a tooth brush (Extra Hard Tooth Brush #306, Butler, U.S.A.) which applied a constant pressure (200 g) at a constant speed (120 strokes per min.) to the specimens. The specimens were weighed by using an electronic toploading balance (Mettler Type PC-440, Mettler Instrumente AG, Switzerland) at 0, 1,000, 3,000, 6,000, 12,000, 30,000, 50,000 and 100,000 brushing strokes. These test were repeated 5 times and the measurements were made 2 times in each strokes of each specimen, and the average of them were evaluated. The weight of PTFE coating decreased in 5% at the brushing stroke of 6,000 times, but after then the change was not so noticeable. The degree of decrease of PTFE coating at 100,000 brushing strokes was at most 10% as shown in FIG. 1. Microscopic photographs of the surface of PTFE coating on the specimen before and after the abrasion test were shown in FIG. 2. After 100,000 strokes, PTFE coating was still remained enough on the surface of the specimen, which indicated that PTFE coating showed high resistance against brushing.

TEST EXAMPLE 2

The effect of PTFE coating on the early adhesion of St. mutans in vitro

Figure 3:
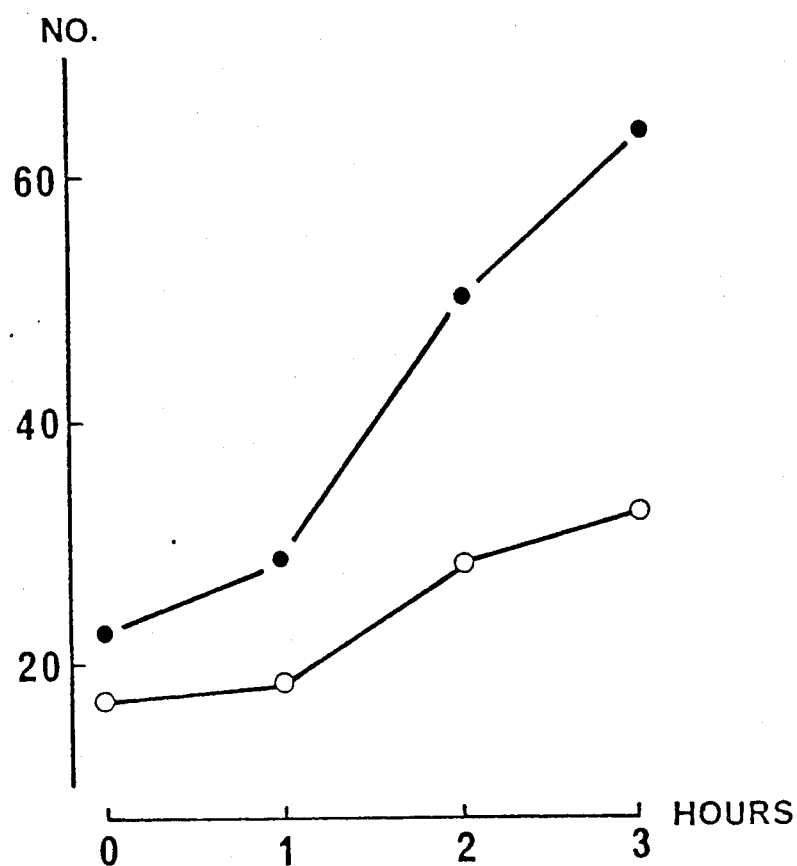
Figure 4:
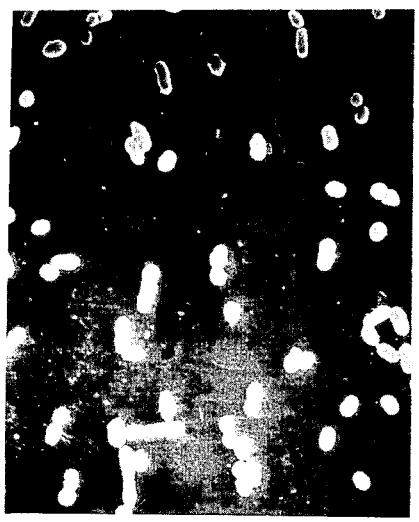
Figure 4:
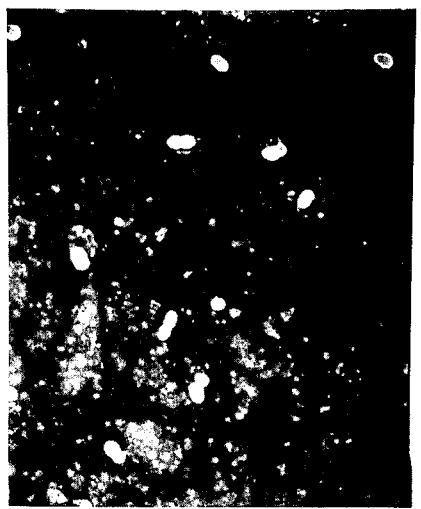

The test solution was obtained from St. mutans (HS-6 strain) overnight culture by the addition of 1/15 M phosphate buffered saline to a final concentration of O.D.=2 and from subsequent ultrasonication for 45 sec. The specimens obtained in Example 1 were immersed in 70 ml of the test solution and were then placed in a shaking bath at 37° C. The test specimens were divided into 3 groups, which were immersed for 1, 2 and 3 hours, respectively. Each specimen was prepared in a conventional manner to enable measurement of the number of adhesive cells by means of a scanning electron microscopy with a magnification of 3,000. Five views were photographed for each specimen and the mean of the number of adhesive cells counted on the photograph was evaluated. As shown in FIG. 3, the number of adhesive cells on the both specimens gradually increased with increase in the incubation time. At each incubation time, a statistical analysis (combined Wilcoxon Ansari-Bradley test) was made on the number of adhesive cells on the both specimens. There were no significant differences at 0 and 1 hour ($P<0.05$). However, at 2 and 3 hours, significant differences were indicated between the number of adhesive cells on the specimens coated with and without PTFE ($P<0.05$). FIG. 4 shows microscopic photographs of the adhesive cells on the both specimens obtained from the incubation for 2 hours. From the photographs, it was evident that the early adhesion of St. mutans was suppressed by PTFE coating in comparison with that of non-coating.

TEST EXAMPLE 3

The effect of PTFE coating on the plaque accumulation in vivo

Figure 5:
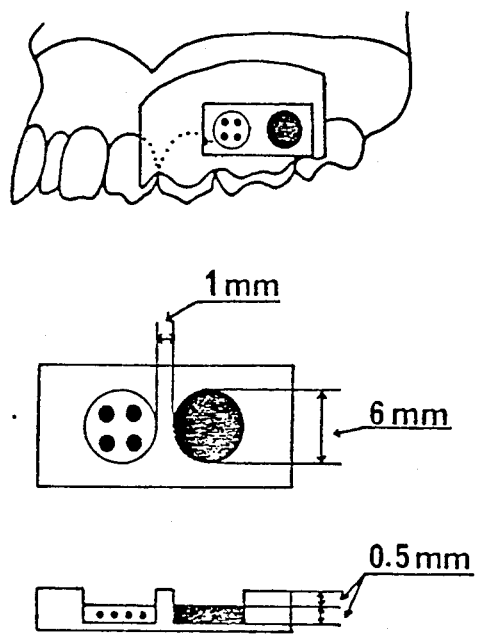
Figure 6:
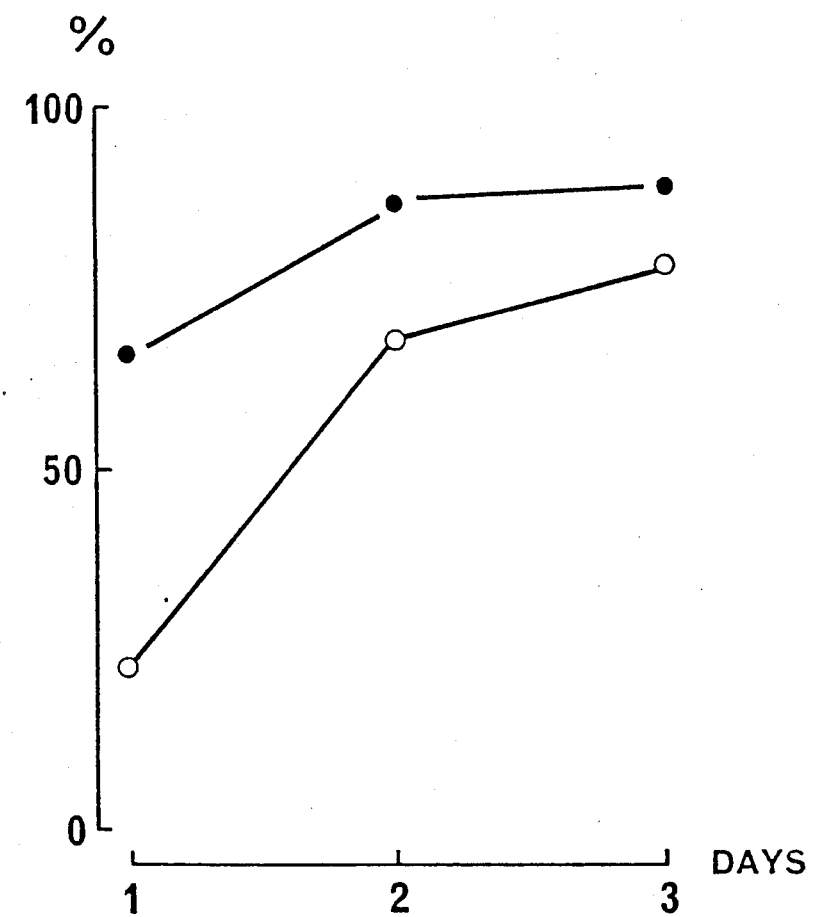

Seventeen healthy volunteers (male) without a history of recent dental care, 24 to 26 years of age, participated in this experiment. A maxillary retainer to hold 2 specimens in the oral cavity was fabricated, on the stone cast, of acrylic resin for each subject. Two specimens made from Au-Pd alloy were prepared as circular discs, 6.0 mm in diameter and 0.5 mm in thickness, and one of them was coated with PTFE coating composition of Example 1. The acrylic resin retainers having the 2 discs were ligated to the buccal surfaces of the upper first molars on both sides in each of 17 subjects (FIG. 5). The mesio-distal positioning of the 2 discs was inverted in each side. The subjects were instructed to continue their usual eating habits and refrain from brushing during the experiment. The test assemblies were inserted for 3 days, and the plaque accumulated on them was stained by using a disclosing solution (Fast Green, Chroma, Stuttgart, West Germany) and was then photographed in every one day. The outline of each specimen was traced, along with the borders of all areas that were estimated to be stained. A compensating polar planimeter (O-back-L, Ushikata Shokai Co., Ltd., Japan) was used to measure the areas of the stained and total surfaces of each specimen. As shown in FIG. 6, the stained surface area of the both specimens increased with increase in the duration of insertion. There was no significant difference at 3 days after insertion ($P<0.05$). However, at 1 and 2 days after insertion, significant differences were indicated between the stained surface areas of the specimens coated with and without PTFE ($P<0.05$).

TEST EXAMPLE 4

The effect of PTFE coating on the removability of the accumulated plaque in vivo Seven healthy volunteers participated in this experiment. By the same method as that of the foregoing experiment, the plaque accumulated, for 3 days, on the specimens were stained and photographed. They were exposed to a running tap water (for 90 sec) issuing from a constant pressure system (Water Pick, Teledyne, U.S.A.) at constant distance of 2 cm, and were restained and rephotographed. As shown in Table I, the plaque was not removed completely in all of the specimen coated with PTFE, but the accumulated plaque areas were remarkably reduced by a running tap water in comparison with those without PTFE. Therefore, it can be considered that the specimen coated with PTFE exhibits good removability of the accumulated plaque as compared with that of non-coating.

The accumulated plaque on the PTFE coating was significantly less at 1 and 2 days after insertion than that without PTFE, but not at 3 days after insertion as apparent from Test Example 3. However, Test Example 4 shows that the removability of the accumulated plaque was significantly higher in the specimens with PTFE even at 3 days after insertion than those without PTFE.

Therefore, it is concluded that if a method such as a combination of brushing and a water issuing device is used clinically to metal casting coated with PTFE just after eating in every days, the beneficial effect of PTFE coating may last for a long time.

TABLE I

Effect of PTFE coating on the removability of the accumulated plaque

| | Removability | | | | |
|---|---|---|---|---|---|
| | Complete | Good | Moderate | Poor | None |
| With PTFE | 4 | 6 | 3 | 1 | 0 |
| Without PTFE | 0 | 0 | 1 | 7 | 6 |

Note:
Complete, 100% removal of the accumulated plaque area; Good, above 80%; Moderate, 50-80%; Poor, below 50%; None, 0%.

We claim:

1. A dental casting coated with a tetrafluoroethylene polymer.

2. A dental casting as defined in claim 1 wherein the dental casting is made from a metal alloy.

3. A dental casting as defined in claim 2 wherein the metal alloy is Au alloy, Ag alloy, Co alloy or Cr alloy.

4. A dental casting coated with a mixture of a fluoroethylene polymer and an adhesive binder selected from the group consisting of polyimide, polyamideimide, epoxy resin, alkyd resin, polyethersulfone, polysulfone and polyphenylene sulfide.

5. A dental casting as defined in claim 4 wherein the adhesive binder is used in an amount of about 0.1 to about 20 parts by weight per one part by weight of tetrafluoroethylene polymer.

6. A dental casting as defined in claim 5 wherein the amount of binder is about 0.3 to about 8 parts by weight per one part by weight of tetrafluoroethylene polymer.

7. A dental casting as defined in claim 1 wherein the tetrafluoroethylene polymer is coated in a thickness of about 0.5 to about 20 μm after baking.

8. A dental casting as defined in claim 7 wherein the thickness is about 1 to about 5 μm after baking.

9. A method of preventing the plaque accumulation on a dental casting comprising coating the casting with a tetrafluoroethylene polymer.

* * * * *